United States Patent [19]

Garret et al.

[11] Patent Number: 5,502,049
[45] Date of Patent: Mar. 26, 1996

[54] USE OF PHENOTHIAZINE DERIVATIVES IN THE TREATMENT OF ISCHAEMIA AND/OR HYPOXIA

[75] Inventors: Claude Garret, Fontenay sous Bois; Jean Rataud, Eaubonne; Jean-Marie Stutzmann, Villecresnes, all of France

[73] Assignee: Rhone-Poulenc Rorer S.A., Antony, France

[21] Appl. No.: 295,667

[22] PCT Filed: Mar. 29, 1993

[86] PCT No.: PCT/FR93/00312

§ 371 Date: Sep. 7, 1994

§ 102(e) Date: Sep. 7, 1994

[87] PCT Pub. No.: WO93/19757

PCT Pub. Date: Oct. 14, 1993

[30] Foreign Application Priority Data

Mar. 30, 1992 [FR] France .................................... 92 03793

[51] Int. Cl.⁶ .................................................. A61K 31/54
[52] U.S. Cl. .................... 514/224.8; 514/225.2; 514/225.5; 514/226.2
[58] Field of Search ............... 514/224.8, 225.2, 514/225.5, 226.2

[56] References Cited

U.S. PATENT DOCUMENTS

| 3,112,310 | 11/1963 | Skokie et al. | 544/44 |
| 4,833,138 | 5/1989 | Olney | 514/226.2 |
| 5,049,669 | 9/1991 | Garret et al. | 514/226.2 |

FOREIGN PATENT DOCUMENTS 0419360  3/1991  European Pat. Off. .

OTHER PUBLICATIONS

Tribulova et al., "Effect of chlorpromazine on the extent of ischemic changes of the myocardium. A histochemical study", Histochem. J. 16 383–384 (1984).

"Effetto preventivo di composti fenotiazinici e tioxantenici sulla necrosi epatica sperimentale da ischemia", Ann. Ist. Super. Sanita 7, 601–604 (1971).

G. E. Thomas et al., "Chlorpromazine Inhibits Loss of Contractile Function, Compliance and ATP in Ischemic Rabbit Heart", J Mol Cell Cardiol 15, 621–628 (1983).

*Primary Examiner*—Marianne M. Cintins
*Assistant Examiner*—Kevin E. Weddington
*Attorney, Agent, or Firm*—Finnegan, Henderson, Farabow, Garrett & Dunner

[57] ABSTRACT

This invention relates to a novel therapeutical use of phenzothiazine derivatives of general formula (I),

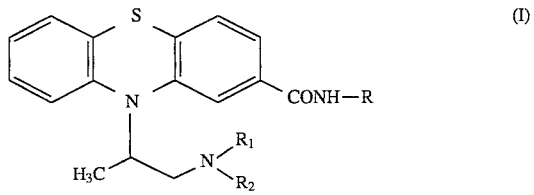

wherein R is a straight or branched chain $C_{1-5}$ alkyl radical, and $R_1$ and $R_2$, which are the same or different, are $C_{1-2}$ alkyl radicals or form, together with the nitrogen atom to which they are attached, a pyrrolidinyl radical; and salts and stereoisomers thereof; having useful prophylactic and/or curative activity for the treatment of ischaemia and/or hypoxia.

2 Claims, No Drawings

USE OF PHENOTHIAZINE DERIVATIVES IN THE TREATMENT OF ISCHAEMIA AND/OR HYPOXIA

This application is a 371 of PCT/FR 43/00312 filed Mar. 29, 1993.

FIELD OF THE INVENTION

The present invention relates to a novel therapeutic application of the phenothiazine derivatives of general formula:

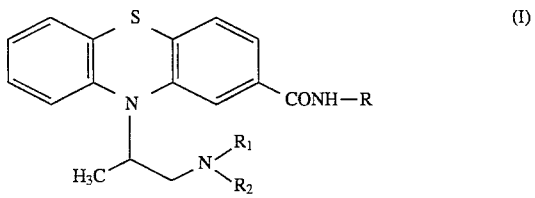

(I)

in which:
the symbol R is an alkyl radical containing 1 to 5 carbon atoms in a straight or branched chain, and the symbols $R_1$ and $R_2$, which may be identical or different, are alkyl radicals containing 1 or 2 carbon atoms, or, together with the nitrogen atom to which they are attached, form a pyrrolidinyl radical, as well as their salts.

BACKGROUND OF THE INVENTION

It is understood that the products of general formula (I) exist in stereoisomeric forms, and that these stereoisomeric forms as well as the mixtures thereof fall within the scope of the present invention.

The phenothiazine derivatives which form the subject of the present invention are known for their analgesic and diuretic activity, as well as for their activity with respect to the central nervous system: U.S. Pat. No. 5,049,669 and U.S. Pat. No. 3,112,310.

DESCRIPTION OF THE INVENTION

It has now been found that a subclass of previously known phenothiazine derivatives, as well as their salts, additionally possess activity in the treatment of hypoxia and/or ischaemia. This subclass is defined by the general formula (I).

It was possible to demonstrate the activity of the products of general formula (I) in the method of N-methyl-DL-aspartic acid(NMDLA)-induced fits.

There is, in effect, a large amount of experimental data indicating that the excitatory neuromediator glutamate is a neurotoxin, and that the N-methyl-D-aspartate (NMDA) glutamate receptor (one of the glutamatergic receptors) complex is involved in the pathology of cerebral ischaemia.

It has been clearly demonstrated that NMDA antagonists manifest protective activity with respect to the damage caused by cerebral ischaemia or hypoxia: U. Dirnagl, J. Tanabe and W. Pulsinelli, Brain Research, 527, 62 (1990).

The phenothiazine derivatives of general formula (I), as well as their salts, are entirely suitable for the preparation of a medicinal product intended for the preventive and/or curative treatment of ischaemia and/or hypoxia, and in the following indications in particular:

haemorrhagic or embolic cerebrovascular accidents;
subarachnoid haemorrhage;
cranial trauma with cerebral involvement;
epileptic seizure state with cerebral involvement;
state of cerebral ischaemia due to cerebral disturbance during carotid endarterectomy or during surgery necessitating an extracorporeal circulation;
radiotherapy of cerebral tumours (neuroprotection);
treatment of acute mountain sickness;

Experimental Study

The activity was demonstrated in the following test, adapted from Singh, L. et al., Brit. J. Pharmacol., 99, 285 (1990).

Fits induced by N-methyl-DL-aspartic acid (NMDLA):

The salt of N-methyl-DL-aspartic acid (NMDLA) at a concentration of 42.5 mg/cm$^3$ is injected intravenously (i.v.) (0.14 cm$^3$/min) into the tail vein of a mouse (CD1 male, Charles River) until a convulsion is produced.

This convulsion represents the end-point of the test, and the mouse is killed immediately after the onset of this convulsion. The time elapsing between the injection of NMDLA and the fit is measured, and the threshold dose of NMDLA required to produce this fit is calculated for each mouse.

For the antagonists, the products under study are administered subcutaneously, 30 minutes before the injection of NMDLA at the threshold dose needed to introduce a fit. The results are expressed as a percentage increase in the time of onset of the fit, by comparison with the control group (which received only NMDLA), according to the following formula.

threshold dose of NMDLA in the treated group×100−100
threshold dose of NMDLA in the control group The minimum active dose is the first dose significantly different from the control which corresponds to a value of the above ratio of greater than 20.

It was demonstrated that the active doses lie in a range between 1 and 3 mg/kg.

The results obtained appear in the table below.

| Example No. | Structure | % increase in the time of onset of convulsions at a dose of 3 mg/kg s.c. |
|---|---|---|
| 1 | phenothiazine-N-CH(CH₃)CH₂-pyrrolidine, with CONH—nC₄H₉ substituent | 41 |
| 2 | phenothiazine-N-CH(CH₃)CH₂-N(C₂H₅)₂, with CONH—CH₂CH₂CH(CH₃)₂ substituent | 28.5 |
| 3 | phenothiazine-N-CH(CH₃)CH₂-pyrrolidine, with CONH—nC₃H₇ substituent (L Series) | 64 |
| 4 | phenothiazine-N-CH(CH₃)CH₂-pyrrolidine, with CONH—nC₃H₇ substituent | 28 |
| 5 | phenothiazine-N-CH(CH₃)CH₂-pyrrolidine, with CONH—CH₂CH(CH₃)₂ substituent (L Series) | 61 |
| 6 | phenothiazine-N-CH(CH₃)CH₂-pyrrolidine, with CONH—CH₂CH₂CH(CH₃)₂ substituent (L Series) | 28 |

| Example No. | Structure | % increase in the time of onset of convulsions at a dose of 3 mg/kg s.c.. |
|---|---|---|
| 7 | 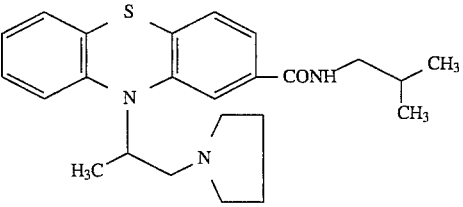 (L Series) | 24 |

Of special importance for their anti-ischaemic activity are the products of general formula (I) for which the symbol R is an alkyl radical containing 3 to 5 carbon atoms in a straight or branched chain, and symbols $R_1$ and $R_2$ represent ethyl radicals or, with the nitrogen atom to which they are attached, form a pyrrolidinyl radical.

And among these products, the preferred products are mainly those mentioned below.

—N-n-propyl-10-[1-(1-pyrrolidinyl)-2-propyl]-2-phenothiazinecarboxamide, in its stereoisomeric forms and the mixtures thereof, as well as its salts;

—N-(3-methylbutyl)-10-[1-diethylamino-2-propyl]-2-phenothiazinecarboxamide, in its stereoisomeric forms and the mixtures thereof, as well as its salts;

—N-(3-methylbutyl)-10-[1-(1-pyrrolidinyl)-2-propyl]-2-phenothiazinecarboxamide, in its stereoisomeric forms and the mixtures thereof, as well as its salts;

—N-n-butyl-10-[1-(1-pyrrolidinyl)-2-propyl]-2-phenothiazinecarboxamide, in its stereoisomeric forms and the mixtures thereof, as well as its salts;

—N-i-butyl-10-[1-(1-pyrrolidinyl)-2-propyl]-2-phenothiazinecarboxamide, in its stereoisomeric forms and the mixtures thereof, as well as its salts;

—N-(2-methylbutyl)-10-[1-(1-pyrrolidinyl)-2propyl]-2-phenothiazinecarboxamide, in its stereoisomeric forms and the mixtures thereof, as well as its salts.

The preparation of the products of general formula (I) has been described in U.S. Pat. No. 5,049,669.

The present invention relates to the production of a medicinal product containing at least one product of general formula (I), optionally in salt form, in the pure state or in the form of a pharmaceutical composition in combination with any other pharmaceutically acceptable and compatible diluent or adjuvant.

The compositions according to the invention may be used parenterally or orally for preventive and/or curative purposes.

The sterile compositions for parenteral administration which can be, in particular, used in the form of perfusions are preferably suspensions, emulsions or aqueous or non-aqueous solutions.

As a solvent or vehicle, water, propylene glycol, a polyethylene glycol, vegetable oils, especially olive oil, injectable organic esters, for example ethyl oleate, or other suitable organic solvents may be employed. These compositions can also contain adjuvants, especially wetting, tonicity, emulsifying, dispersing and stabilizing agents. The sterilization may be carried out in several ways, for example by aseptic filtration, by incorporating sterilizing agents in the composition, by irradiation or by heating. They may also be prepared in the form of sterile solid compositions which may be dissolved at the time of use in a sterile injectable medium.

As solid compositions for oral administration, tablets, hard gelatin capsules, powders or granules may be used.

In these compositions, the active principle according to the invention (optionally combined with another pharmaceutically compatible product) is mixed with one or more inert diluents or adjuvants such as sucrose, lactose or starch.

These compositions can also comprise substances other than diluents, for example a lubricant such as magnesium stearate.

As solid compositions for oral administration, emulsions which are pharmaceutically acceptable, solutions, suspensions, syrups and elixirs containing inert diluents such as water or liquid paraffin may be used. These compositions can also comprise substances other than diluents, for example wetting, sweetening or flavoring products.

In human therapy, the products according to the invention are especially useful in the treatment or prevention of haemorrhagic or embolic cerebrovascular accidents, subarachnoid haemorrhage, cranial trauma with cerebral involvement, state of cerebral ischaemia due to cerebral disturbance in fits of carotid endarterectomy or during surgery necessitating an extracorporeal circulation, neuroleptic seizure state with cerebral involvement, radiotherapy of cerebral tumours (Neuroprotection) and treatment of acute mountain sickness.

The doses depend on the effect sought and the treatment period.

For an adult, they are generally between 0.005 to 1 mg/kg i.v. per day.

Generally speaking, the doctor will determine the dosage he considers most suitable in accordance with the age and weight and all other factors specific to the subject to be treated.

EXAMPLES

The example which follows, given without implied limitation, illustrates a composition according to the invention:

Example

A solution for intravenous administration containing 25 mg/cm$^3$ of active product (base) is prepared according to the usual technique:

| | |
|---|---|
| N-n-Propyl-10-[1-(1-pyrrolidinyl)-2-propyl]-2-phenothiazinecarboxamide | 2.70 g |

| | |
|---|---:|
| hydrochloride, L series | |
| Ascorbic acid | 0.100 g |
| Neutral sodium sulphite | 0.050 g |
| 1N sodium hydroxide | approximately 0.08 cm³ |
| NaCl | approximately 0.650 g |
| water for injections | q.s. 100 cm³ |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Method for treatment of ischaemia and/or hypoxia comprising treating a patient with an effective amount of N-n-propyl-10-(1-(1-pyrrolidinyl)-2-propyl)-2-phenothiazinecarboxamide (L series) or their pharmaceutically acceptable salts.

2. Method for treatment of ischaemia and/or hypoxia comprising treating a patient with an effective amount of N-(2-methylbutyl)-10-(1-(1-pyrrolidinyl)-2-propyl)-2-phenothiazinecarboxamide (L series) or their pharmaceutically acceptable salts.

* * * * *